(12) United States Patent
Levine (10) Patent No.: US 8,304,219 B2
(45) Date of Patent: *Nov. 6, 2012

(54) KLUYVEROMYCES STRAINS METABOLIZING CELLULOSIC AND HEMICELLULOSIC MATERIALS

(75) Inventor: Robert Paul Levine, Palo Alto, CA (US)

(73) Assignee: Phage Pharmaceuticals, Inc., San Diego, CA (US)

( * ) Notice: Subject to any disclaimer, the term of this patent is extended or adjusted under 35 U.S.C. 154(b) by 1187 days.

This patent is subject to a terminal disclaimer.

(21) Appl. No.: 12/024,889

(22) Filed: Feb. 1, 2008

(65) Prior Publication Data

US 2008/0193992 A1    Aug. 14, 2008

Related U.S. Application Data

(62) Division of application No. 10/759,785, filed on Jan. 16, 2004, now Pat. No. 7,344,876.

(60) Provisional application No. 60/442,455, filed on Jan. 24, 2003.

(51) Int. Cl.
*C12P 7/06* (2006.01)

(52) U.S. Cl. ........................ 435/161; 435/255.1; 435/171

(58) Field of Classification Search ..................... None
See application file for complete search history.

(56) References Cited

U.S. PATENT DOCUMENTS 6,271,007 B1    8/2001    Apajalahti et al.

OTHER PUBLICATIONS

Margaritis, et al. "Effect of Sugar Concentration in Jerusalem Artichoke Extract on *Kluyveromyces marxianus* Growth and Ethanol Production," *Applied and Environmental Microbiology*, vol. 45, No. 2, pp. 723-725, Feb. 1983.

Barron, et al. "Ethanol Production by *Kluyveromyces marxianus* IMB3 During Growth on Straw-Supplemented Whiskey Distillery Spent Wash at 45° C.," *Bioprocess Engineering*, vol. 17, pp. 383-386, 1997.

Morikawa, et al. "Ethanol Productions from D-Xylose and Cellobiose by *Kluyveromyces cellobiovorus*," *Biotechnology and Bioengineering*, vol. 37, pp. 509-513, 1985.

Nilsson, et al. "The Effects of Phosphoric Acid Pretreatment on Conversion of Cellulose to Ethanol at 45° C. Using the Thermotolerant Yeast *Kluyveromyces marxianus* IMB3," *Biotechnology Letters*, vol. 17, No. 9, pp. 985-988, Sep. 1995.

*Primary Examiner* — Irene Marx
(74) *Attorney, Agent, or Firm* — McDonnell Boehnen Hulbert & Berghoff LLP (57) ABSTRACT

This invention relates to the use of microorganisms for the generation of ethanol from lignocellulosic waste materials. Yeast strains of the genus *Kluyveromyces* which have the capability to ferment cellulose, hexose sugars to ethanol are provided. Also provided are methods for converting cellulose, hexoses, or mixed hydrolysates of hexoses to ethanol by fermentation with *Kluyveromyces* strains. The invention also provides methods to isolate yeast strains which metabolize cellulose, pentoses, or hemicelluloses from waste materials.

14 Claims, 7 Drawing Sheets

FIG. 1A

D1/D2 26S RIBOSOMAL DNA SEQUENCE IDENTIFYING SSSJ-0 AS AN
ISOLATE OF KLUYVEROMYCES MARXIANUS

```
SSSJ-0                    ---CCAACCGGGATNGCCTTNGTAACGGCGAGTGAAGCGGCAAAAGCTCA  47
Kluyveromyces marxianus   AAACCAACCGGGATTGCCTTAGTAACGGCGAGTGAAGCGGCAAAAGCTCA  50
Kluyveromyces lactis      AAACCAACCGGGATTGCCTTAGTAACGGCGAGTGAAGCGGCAAAAGCTCA  50
Kluyveromyces wickerhamii AAACCAACCGGGATTGCCTTAGTAACGGCGAGTGAAGCGGCAAAAGCTCA  50
Kluyveromyces dobzhanskii AAACCAACCGGGATTGCCTTAGTAACGGCGAGTGAAGCGGCAAAAGCTCA  50
                             ************************************************

SSSJ-0                    AATTTGAAATCTGGCGTCTTCGACGTCCGAGTTGTAATTTGAAGAAGGCG   97
Kluyveromyces marxianus   AATTTGAAATCTGGCGTCTTCGACGTCCGAGTTGTAATTTGAAGAAGGCG  100
Kluyveromyces lactis      AATTTGAAATCTGGCGTCTTCGACGTCCGAGTTGTAATTTGAAGAAGGCA  100
Kluyveromyces wickerhamii AATTTGAAATCTGGCGTCTTCGACGTCCGAGTTGTAATTTGAAGAAGGTA  100
Kluyveromyces dobzhanskii AATTTGAAATCTGGCGTCTTCGACGTCCGAGTTGTAATTTGAAGAAGGTT  100
                          *********************************************

SSSJ-0                    ACTTTGTAGCTGGTCCTTGTCTATGTTCCTTGGAACAGGACGTCATAGAG  147
Kluyveromyces marxianus   ACTTTGTAGCTGGTCCTTGTCTATGTTCCTTGGAACAGGACGTCATAGAG  150
Kluyveromyces lactis      ACTTTGTAGCTGGTCCTTGTCTATGTTCCTTGGAACAGGACGTCATAGAG  150
Kluyveromyces wickerhamii ACTTTGTAGCTGGTCCTTGTCTATGTTCCTTGGAACAGGACGTCATAGAG  150
Kluyveromyces dobzhanskii ACTTTGTAGCTGGTCCTTGTTTATGTTCCTTGGAACAGGACGTCATAGAG  150
                          ******************** *****************************

SSSJ-0                    GGTGAGAATCCCGTGTGGCGAGGATCCCAGTTATTTGTAAAGTGCTTTCG  197
Kluyveromyces marxianus   GGTGAGAATCCCGTGTGGCGAGGATCCCAGTTATTTGTAAAGTGCTTTCG  200
Kluyveromyces lactis      GGTGAGAATCCCGTGTGGCGAGGATCCCAGTTATTTGTAAAGTGCTTTCG  200
Kluyveromyces wickerhamii GGTGAGAATCCCGTGTGGCGAGGATCCCAGTTATATGTAAAGTGCTTTCG  200
Kluyveromyces dobzhanskii GGTGAGAATCCCGTGTGGCGAGGATACCAGTTATATGTAAAGTACTTTCG  200
                          *************************  *******  *******  *****

SSSJ-0                    ACGAGTCGAGTTGTTTGGGAATGCAGCTCTAAGTGGGTGGTAAATTCCAT  247
Kluyveromyces marxianus   ACGAGTCGAGTTGTTTGGGAATGCAGCTCTAAGTGGGTGGTAAATTCCAT  250
Kluyveromyces lactis      ACGAGTCGAGTTGTTTGGGAATGCAGCTCTAAGTGGGTGGTAAATTCCAT  250
Kluyveromyces wickerhamii ACGAGTCGAGTTGTTTGGGAATGCAGCTCTAAGTGGGTGGTAAATTCCAT  250
Kluyveromyces dobzhanskii ACGAGTCGAGTTGTTTGGGAATGCAGCTCTAAGTGGGTGGTAAATTCCAT  250
                          **************************************************

SSSJ-0                    CTAAAGCTAAATATTGGCGAGAGACCGATAGCGAACAAGTACAGTGATGG  297
Kluyveromyces marxianus   CTAAAGCTAAATATTGGCGAGAGACCGATAGCGAACAAGTACAGTGATGG  300
Kluyveromyces lactis      CTAAAGCTAAATATTGGCGAGAGACCGATAGCGAACAAGTACAGTGATGG  300
Kluyveromyces wickerhamii CTAAAGCTAAATATTGGCGAGAGACCGATAGCGAACAAGTACAGTGATGG  300
Kluyveromyces dobzhanskii CTAAAGCTAAATATTGGCGAGAGACCGATAGCGAACAAGTACAGTGATGG  300
                          **************************************************

SSSJ-0                    AAAGATGAAAAGAACTTTGAAAAGAGAGTGAAAAAGTACGTGAAATTGTT  347
Kluyveromyces marxianus   AAAGATGAAAAGAACTTTGAAAAGAGAGTGAAAAAGTACGTGAAATTGTT  350
Kluyveromyces lactis      AAAGATGAAAAGAACTTTGAAAAGAGAGTGAAAAAGTACGTGAAATTGTT  350
Kluyveromyces wickerhamii AAAGATGAAAAGAACTTTGAAAAGAGAGTGAAAAAGTACGTGAAATTGTT  350
Kluyveromyces dobzhanskii AAAGATGAAAAGAACTTTGAAAAGAGAGTGAAAAAGTACGTGAAATTGTT  350
                          **************************************************

SSSJ-0                    GAAAGGGAAGGGCATTTGATCAGACATGGCGTTTGCTTCGGCTTTCGCTG  397
Kluyveromyces marxianus   GAAAGGGAAGGGCATTTGATCAGACATGGCGTTTGCTTCGGCTTTCGCTG  400
Kluyveromyces lactis      GAAAGGGAAGGGCATTTGATCAGACATGGCGTTTGCTTCGGCTTTCGCTG  400
Kluyveromyces wickerhamii GAAAGGGAAGGGCATTTGATCAGACATGGCGTTTGCTTCGGCGTTCGCTG  400
Kluyveromyces dobzhanskii GAAAGGGAAGGGCATTTGATCAGACATGGCGTTTGCTTCGGCTTTCGCTG  400
                          ****************************************** *******

SSSJ-0                    GGCCAGCATCAGTTTTAGCGGTTGGATAAATCCTCGGGAATGTGGCTCTG  447
Kluyveromyces marxianus   GGCCAGCATCAGTTTTAGCGGTTGGATAAATCCTCGGGAATGTGGCTCTG  450
Kluyveromyces lactis      GGCCAGCATCAGTTTTAGCGGTTGGATAAATCCTCGGGAATGTGGCTCTG  450
Kluyveromyces wickerhamii GGCCAGCATCAGTTTTAGCGGTTGGATAAATCCTCGGGAATGTAGCTCTA  450
Kluyveromyces dobzhanskii GGCCAGCATCAGTTTTGCGGCTGGATAAATCCTCGGGAATGTGGCTCTA  450
                          ****************  ***  *********************  *****

SSSJ-0                    CTTCGGTAGAGTGTTATAGCCCGTGGGAATACAGCCAGCTGGGACTGAGG  497
```

FIG. 1B

| | |
|---|---|
| Kluyveromyces marxianus | CTTCGGTAGAGTGTTATAGCCCGTGGGAATACAGCCAGCTGGGACTGAGG 500 |
| Kluyveromyces lactis | CTTCGGTAGAGTGTTATAGCCCGTGGGAATACAGCCAGCTGGGACTGAGG 500 |
| Kluyveromyces wickerhamii | CCTCGGTAGAGTGTTATAGCCCGTGGGAATACAGCCAGCTGGGACTGAGG 500 |
| Kluyveromyces dobzhanskii | CCGTGGTAGAGTGTTATAGCCCGTGGGAATACAGCCAGCTGGGACTGAGG 500 |
| | *  ************************************************ |
| | |
| SSSJ-0 | ATTGCGACTTTTGTCAAGGATGCTGGCGTAATGGTTAAATGCCGC 542 |
| Kluyveromyces marxianus | ATTGCGACTTTTGTCAAGGATGCTGGCGTAATGGTTAAATGCCGC 545 |
| Kluyveromyces lactis | ATTGCGACTTTTGTCAAGGATGCTGGCGTAATGGTTAAATGCCGC 545 |
| Kluyveromyces wickerhamii | ATTGCGACTTTTGTCAAGGATGCTGGCGTAATGGTTAAATGCCGC 545 |
| Kluyveromyces dobzhanskii | ATTGCGACTTTTGTCAAGGATGCTGGCGTAATGGTTAAATGCCGC 545 |
| | ********************************************* |

KLUYVEROMYCES STRAINS METABOLIZING CELLULOSIC AND HEMICELLULOSIC MATERIALS

CROSS-REFERENCES TO RELATED APPLICATIONS

This application is a divisional of U.S. application Ser. No. 10/759,785, filed Jan. 16, 2004 which claims priority to provisional Application No. 60/442,455, filed Jan. 24, 2003 which are both incorporated herein by reference.

STATEMENT AS TO RIGHTS TO INVENTIONS MADE UNDER FEDERALLY SPONSORED RESEARCH AND DEVELOPMENT

Not applicable.

REFERENCE TO A "SEQUENCE LISTING," A TABLE, OR A COMPUTER PROGRAM LISTING APPENDIX SUBMITTED ON A COMPACT DISK

A sequence listing is included herewith at pages 25-27.

FIELD OF THE INVENTION

This invention relates to the use of microorganisms for the generation of ethanol from cellulosic waste materials. Novel yeast strains of the genus *Kluyveromyces* which have the capability to ferment cellulose, or hexose sugars to ethanol are provided. Also provided are methods for converting cellulose, or mixed hydrolysates of hexoses to ethanol by fermentation with *Kluyveromyces* strains. The invention also provides methods to isolate yeast strains which metabolize cellulose, hexoses, pentoses, or hemicelluloses from waste materials.

BACKGROUND OF THE INVENTION

Ethanol provides a favorable alternative to the use of fossil fuels for energy generation, and increased use of ethanol for fuel could reduce dependence on fossil fuels as well as decrease the accumulation of carbon dioxide in the atmosphere. In the United States, biological production of ethanol, principally by fermentation of grain starches and sugars by yeast, is over four billion liters per year. However, cellulosic biomass potentially provides a far more abundant source of ethanol. Cellulosic biomass represents the greatest carbohydrate resource on earth, and is fixed photosynthetically at a rate of about $10^{11}$ tons per year globally.

Conversion of cellulosic biomass to ethanol requires that the polysaccharides of the biomass first be hydrolyzed to fermentable monosaccharides. Cellulose is a polymer of glucose units, and, while hydrolysis of cellulose is more difficult than hydrolysis of starches, hydrolysis of cellulose yields glucose that is readily fermented by yeasts such as *Saccharomyces cerevisiae* and *Kluyveromyces marxianus*. However, cellulosic biomass comprises, in addition to cellulose, more complex and heterogeneous polymers collectively known as hemicellulose. Unlike cellulose, hemicellulose contains saccharides besides glucose—principally the pentose xylose, as well as the pentose arabinose and the hexoses glucose, galactose, and mannose. The pentose content of some cellulosic biomass may reach as high as 35% of the total carbohydrate content (see Rosenberg, *Enzyme Microbiol Technol* 2:185-193 (1980)). Moreover, in many industrial processes, hemicellulose is hydrolyzed to monosaccharides more efficiently than cellulose. Thus, 35-50% of the fermentable sugars obtained by enzymatic or chemical hydrolysis of cellulosic materials may be derived from hemicellulose, and much of this sugar may be in the form of xylose or arabinose (Harris et al., USDA Forest Products Laboratory General Technical Report FPL-45 (1985)).

Ideally, biological production of ethanol from cellulosic biomass would employ a natural organism capable of efficiently fermenting all five of the most abundant monosaccharides liberated by hydrolysis of cellulose and hemicellulose—glucose, galactose, mannose, xylose, and arabinose—as well as the disaccharide cellobiose produced by enzymatic digestion of cellulose. Even more ideally, such an organism would be able to hydrolyze resilient polymers such as cellulose or hemicellulose without the addition of exogenous enzymes or chemicals.

No such organism is presently known. In particular, while many yeasts will assimilate pentose sugars and hexose sugars, conversion of pentose- and hexose-containing cellulose or hemicellulose to ethanol by yeasts is problematic (see Jeffries & Kurtzman, *Enzyme Microb Technol* 16:922-932 (1994); Schneider, *Crit Rev Biotechnol* 9:1-40 (1989)). Fermentation of arabinose to ethanol is almost unknown (see Dien et al., *Appl Biochem Biotechnol* 57-58:233-42 (1996); McMillan & Boynton, *Appl Biochem Biotechnol* 45-46:569-84 (1994)). A few yeasts capable of fermenting xylose have been isolated, but their thermotolerance, ability to ferment xylose anaerobically, and their metabolism of hexose sugars are unsatisfactory (see Jeffries & Kurtzman, supra).

Yeasts of the genus *Kluyveromyces*—particularly thermotolerant strains—have many properties making them well-suited for biological production of ethanol (see Banat et al., *World J Microbiol Biotechnol* 14:809-21 (1998); Singh et al., *World J Microbiol Biotechnol* 14:823-34 (1998)). *Kluyveromyces* strains assimilate pentose sugars. However, efficient fermentation of hexoses by *Kluyveromyces* strains has not been described. A single report of high xylose production by *K. marxianus* has appeared (Margaritis & Bajpai, *Appl Environ Microbiol* 44:1039-41 (1982)), but ethanol production was under aerobic conditions and no subsequent report has verified these findings. Other publications report little (Banat et al., supra) or no (Boyle et al., *Biotechnol Lett* 19:49-51 (1997)) ethanol production from xylose by *K. marxianus*, even under aerobic conditions.

U.S. Pat. No. 4,472,501 describes a yeast called *Kluyveromyces cellobiovorus* with the ability to ferment xylose and cellobiose to ethanol, but subsequent analysis of this strain has shown that it does not belong to the genus *Kluyveromyces*, but rather is an isolate of *Candida intermedia* (see Molnar et al., *Antonie Van Leeuwenhoek* 70:67-78 (1996); Ando et al., *Biosci Biotechnol Biochem* 60:1063-9 (1996); Martini & Martini, *Antonie Van Leeuwenhoek* 61:57-60 (1992)).

Thus, no *Kluyveromyces* strain capable of hydrolyzing cellulose has been described. There is a need in the art for thermotolerant organisms capable of both hydrolyzing cellulosic materials, and of efficiently fermenting the hexoses found in hydrolysates to ethanol. The present invention meets these and other needs.

BRIEF SUMMARY OF THE INVENTION

In one aspect, this invention provides biologically pure cultures of yeasts of the genus *Kluyveromyces*, which grow in media comprising pentose sugars or cellulose as the sole carbon source. In one embodiment of the invention, the biologically pure culture is able to grow in a medium comprising as its sole carbon source a pentose selected from the group consisting of xylose or L-arabinose. In some embodiments, the yeast of the biologically pure culture is of the species *Kluyveromyces marxianus*. In a further embodiment, the yeast has the identifying characteristics of *K. marxianus* strain SSSJ-0. In another embodiment of the invention, the biologically pure *Kluyveromyces* culture is capable of fermenting hexose sugars such as glucose, mannose, galactose, and combinations thereof, to ethanol, under either aerobic or anaerobic conditions. In some embodiments, the culture ferments hextose sugars to ethanol at about 43° C. in a defined medium composed of about 20 g/L of the hexose, about 0.67 g/L yeast nitrogen base, and about 0.25 mM magnesium sulfate in a buffer of about 50 mM citrate, pH about 4.5, and fermentation proceeds until at least about 10%, 20%, 30%, 40%, 50%, 60%, 70%, 80%, 90%, or essentially 100% of the available hexose is converted to ethanol.

The invention also provides novel biologically pure cultures of yeasts of the genus *Kluyveromyces*, which have the novel property of being capable of growth in media comprising cellulose and cellulose derivatives as the sole carbon source. This cellulose or cellulose derivative may be a variety of soluble or insoluble pure substrates, such as carboxymethylcellulose, AVICEL® (microcrystalline cellulose), or SIGMACELL® (a high purity cellulose powder); alternatively, the cellulose or cellulose derivative may be comprised in a more complex mixture such as the material found in sludges from paper making and recycling, spent grains from brewing operations, sugared lignin hydrolysates, and corn stover hydrolysates. In some embodiments, the yeast of the biologically pure culture is of the species *Kluyveromyces marxianus*. In a further embodiment, the yeast has the identifying characteristics of *K. marxianus* strain SSSJ-0. In another embodiment of the invention, the biologically pure *Kluyveromyces* culture is capable of fermenting cellulose or a cellulose derivative to ethanol without the addition of exogenous cellulases, under either aerobic or anaerobic conditions. In some embodiments, the culture ferments cellulose or a cellulose derivative to ethanol at about 43° C. in a defined medium composed of about 20 g/L dry weight of cellulose or cellulose derivative, about 0.67 g/L yeast nitrogen base, and about 0.25 mM magnesium sulfate in a buffer of about 50 mM citrate, pH about 4.5, and fermentation proceeds until at least about 10%, 20%, 30%, 40%, 50%, 60%, 70%, 80%, 90%, or essentially 100% of the available cellulose is converted to ethanol.

In another aspect, the invention provides a method of producing ethanol from an aqueous medium comprising a carbon source selected from the group consisting of cellobiose, glucose, mannose, and galactose. The method comprises the steps of contacting the aqueous medium with a biologically pure culture of yeast capable of proliferation in a medium comprising a hexose as the sole carbon source, and incubating the medium and culture under conditions wherein the carbon source is fermented to ethanol. Such fermentation may be aerobic or anaerobic. In a further embodiment, the ethanol is separated and recovered from the medium following or concurrently with fermentation. In one embodiment, the medium and culture is incubated at a temperature between about 43° C. and about 45° C. In some embodiments of the invention, the biologically pure culture of yeast is of the species *Kluyveromyces marxianus*, while in a further embodiment, the yeast of the biologically pure culture has the identifying characteristics of strain SSSJ-0. Up to 100% of the available sugars may be converted into ethanol, depending on the time allowed and the conditions of fermentation. In some embodiments, however, conversion of the available sugars to ethanol is less than complete, e.g., at least about 90%, 80%, 70%, 60%, 50%, 40%, 30%, 20%, or 10% of the available fermentable saccharides are converted to ethanol. In other embodiments, the conversion of sugars to ethanol is expressed as the maximum rate of ethanol production, e.g., about 0.01, 0.05, 0.1, 0.5, or 1 g per hour per liter.

The invention also provides a method producing ethanol from a medium containing cellulose or a cellulose derivative. The method comprises contacting an aqueous medium containing cellulose or a cellulose derivative with a biologically pure culture of a yeast of the genus *Kluyveromyces* which is capable of growth in a medium containing cellulose as the sole carbon source, and incubating the medium and culture under conditions wherein the cellulose is fermented to ethanol. Fermentation may be aerobic or anaerobic. In a further embodiment, the ethanol is separated and recovered from the medium following or concurrently with fermentation. In one embodiment, the medium and culture is incubated at a temperature between about 43° C. and about 45° C. In some embodiments of the invention, the biologically pure culture of yeast is of the species *Kluyveromyces marxianus*, while in a further embodiment, the yeast of the biologically pure culture has the identifying characteristics of strain SSSJ-0. Up to 100% of the theoretical yield of ethanol obtainable from the cellulose or cellulose derivative may be obtained, although in some embodiments a lesser percentage of the theoretical yield may be obtained, e.g., at least 90%, 80%, 70%, 60%, 50%, 40%, 30%, 20%, or 10% of the theoretical yield. In other embodiments, the conversion of cellulose to ethanol is expressed as the maximum rate of ethanol production, e.g., about 0.01, 0.05, 0.1, 0.5, or 1 g per hour per liter.

The invention also provides a method of isolating a biologically pure culture of yeast capable of growth in a medium comprising a pentose such as arabinose or xylose as the sole carbon source. The method comprises the steps of providing a sample of waste material comprising a yeast, culturing a yeast derived from the waste material in a medium comprising a pentose as the sole carbon source, and isolating a biologically pure culture of the yeast, thereby yielding a biologically pure culture of yeast capable of growth in a medium comprising pentose as the sole carbon source. In one embodiment of the isolation procedure, the procedure further comprises the step of culturing the waste material prior to isolation in an enrichment material that supports the growth of yeast in preference to other microorganisms, e.g., contains a high concentration of glucose or is maintained at low pH. In another embodiment of the invention, the enrichment medium comprises a pentose sugar, thereby enriching for organisms able to metabolize pentoses.

The invention also provides a method of isolating a biologically pure culture of yeast capable of growth in a medium comprising cellulose or a cellulose derivative as the sole carbon source. The method comprises the steps of providing a sample of waste material comprising a yeast, culturing a yeast derived from the waste material in a medium comprising cellulose as the sole carbon source, and isolating a biologically pure culture of the yeast, thereby yielding a biologically pure culture of yeast capable of growth in a medium comprising cellulose as the sole carbon source. In one embodiment of the isolation procedure, the procedure further comprises the step of culturing the waste material prior to isolation in an enrichment material that supports the growth of yeast in preference to other microorganisms, e.g., contains a high concentration of glucose or is maintained at low pH. In one embodiment, the enrichment medium comprises 20% glucose and is at pH 4.5.

The invention also provides a method of isolating a biologically pure culture of yeast capable of growth in a medium comprising a hemicellulose or a hemicellulose derivative as the sole carbon source. The method comprises the steps of providing a sample of waste material comprising a yeast, culturing a yeast derived from the waste material in a medium comprising a hemicellulose as the sole carbon source, and isolating a biologically pure culture of the yeast, thereby yielding a biologically pure culture of yeast capable of growth in a medium comprising a hemicellulose as the sole carbon source. The hemicellulose may be chosen from the group of xylans, glucomannans, galactans, glucans, and xyloglucans. In one embodiment of the isolation procedure, the procedure further comprises the step of culturing the waste material prior to isolation in an enrichment material that supports the growth of yeast in preference to other microorganisms, e.g., contains a high concentration of glucose or is maintained at low pH. In another embodiment, the enrichment medium comprises a pentose, to enrich for yeasts which are able to metabolize pentoses liberated by the hydrolysis of hemicellulose.

DEFINITIONS

"Arabinose" refers to the monosaccharide arabino-pentose and its derivatives, occurring primarily as L-arabinofuranose in xylans and xyloglucans.

"Biologically pure culture" refers to a sample of a microorganism that is physically separated from microorganisms of different characteristics. Thus, biologically pure cultures of an organism are substantially free from other organisms naturally found in association with it or naturally occurring in similar source materials. An example of a biologically pure culture is a vessel containing no organisms other than a clonal population of microorganisms derived from a single founder cell. "Biologically pure culture" also refers to a population of organisms derived from a biologically pure culture. Thus, it contemplated that mixed populations of organisms may be generated by secondarily adding other organisms to an existing biologically pure culture. Such a mixed culture comprises a biologically pure culture of the first organism.

"Cellobiose" refers to the disaccharide 4-O-β-D-glucopyranosyl-D-glucose, typically liberated from cellulose by the action of exo-1,4-β-glucanases on cellulose.

"Cellulose" refers to a linear β1-4 glucan with the pyranose units in the $-^4C_1$ conformation, in natural form having a molecular mass between about 50 and 400 kDa. Processed forms of cellulose may be characterized by a particular degree of crystallization or polymerization (e.g., AVICEL® or SIGMACELL®).

"Cellulose derivative" refers to cellulose characterized by covalent modification (e.g., carboxymethylcellulose).

"Waste material(s)" or "cellulosic waste material(s)" refers to any substance comprising cellulose, hemicellulose, or cellulose and hemicellulose. Suitable cellulosic waste materials include, but are not limited to, e.g., corn stover, corn fiber, rice fiber, wheat straw, oat hulls, brewers spent grains, pulp and paper mill waste, wood chips, sawdust, forestry waste, agricultural waste, bagasse, and barley straw.

"Fermenting" refers to the biological conversion of a carbon source into ethanol by a microorganism. Fermentation may be aerobic or anaerobic. Anaerobic fermentation takes place in a medium or atmosphere substantially free of molecular oxygen.

"Galactose" refers to the monosaccharide galacto-hexose and its derivatives, occurring primarily as D-galactopyranose in xylans and glucomannans.

"Glucose" refers to the monosaccharide gluco-hexose and its derivatives, occurring primarily as D-glucopyranose in cellulose, glucomannans, and xyloglucans.

"Proliferate" or "proliferation" refers to a sustained period of cell division under a particular culture condition. A microorganism is capable of "proliferation" on culture medium if, being placed in the culture medium and having exhausted the nutritional resources carried over from any previous culture medium, the microorganism continues to divide and incorporate components of the culture medium into living material. When used in the context of growth on a particular carbon source, "proliferation" requires the organism to utilize the carbon source for metabolic energy. Thus, an organism may be capable of assimilating a particular carbon source, and even incorporating it into living material, but not utilizing it for metabolic energy. For example, conventional yeast strains may be able to assimilate pentoses and incorporate them into nucleic acids, but do not utilize them in glycolysis, respiration, or fermentation and therefore cannot grow in media containing pentose as a sole carbon source.

"Hemicellulose derivative" refers to a structural component of plant cell walls other than cellulose and lignin, or a derivative thereof. Hemicelluloses are heterogeneous and vary depending on the origin of the plant material, but the most commonly found components include xylans, glucomannans, galactans, glucans, and xyloglucans. Thus, upon hydrolysis, hemicellulose may yield glucose, galactose, mannose, xylose, or arabinose.

"Isolating" refers to a process by which microorganisms are physically separated from other microorganisms with dissimilar characteristics. Isolation may be carried out, for example, by culture under selective conditions which permit the growth only of a microorganism with unique characteristics, or by inoculating culture medium with microorganisms under conditions in which a physically isolated population of cells is generated from a single founder cell (e.g., limiting dilution or colony growth on solid media).

"*Kluyveromyces marxianus*" refers to a species of yeast which, in its naturally occurring form, typically comprises the sequence shown in SEQ ID NO: 1 in the variable D1/D2 domain of its nuclear large subunit (26S) ribosomal DNA.

"Hexose" refers to C6 sugars and their derivatives, which may occur in pyranose or furanose form. The hexoses most commonly found in plant material are glucose, galactose, and mannose.

"Mannose" refers to manno-hexose and its derivatives, occurring primarily as D-mannopyranose in glucomannans.

"Pentose" refers to C5 sugars and their derivatives, which may occur in pyranose or furanose form. The pentoses most commonly found in plant material are arabinose and xylose.

"Saccharide" refers to monomeric, oligomeric, or polymeric aldose and ketose carbohydrates. Monosaccharides exist preferably as cyclic hemiacetals and hemiketals but may also exist in acyclic forms. Stereoisomers of cyclic monosaccharides can exist in α- or β-forms and in D- or L-forms. Saccharides are also found in modified form, either as natural products or as a result of chemical modification during hydrolysis or industrial processing. Saccharide derivatives include those modified by deoxygenation or addition of moieties such as acetyl, amino, or methyl groups. In oligosaccharides and polysaccharides, saccharide monomers are connected by characteristic linkages, e.g., β1-4, α1-6, α1-2, α1-3, or β1-2. In some polymers, such as cellulose, the linkages are uniform throughout the polymer, while in others, primarily hemicellulosic materials, the linkages may be mixed. Short (typically 1-3 saccharide) branched side chains are also present in polysaccharides, typically from hemicellulose.

"Sole carbon source" refers to an organic molecule, often a carbohydrate, in a culture medium wherein the molecule is the only significant source of metabolic energy available to the microorganism. Thus, the sole carbon source is the only molecule in the medium available to be utilized to ultimately yield ATP by processes such as glycolysis, respiration, and fermentation. Typically, the sole carbon source will account for at least 95%, usually more than 99% by weight of carbohydrate. Typically, culture media comprise other organic molecules besides a "carbon source" (e.g., those found in yeast nitrogen base), but these organic molecules either cannot be metabolized for energy or are present in too low of a concentration to support the continued growth and metabolism of the culture.

"SSSJ-0" refers to a strain of *K. marxianus* isolated by the methods of the invention and possessing the ability to convert cellulose to ethanol without the addition of exogenous enzymes. The strain was deposited as ATCC No. PTA-3567 on Jul. 26, 2001 in the yeast collection of the American Type Culture Collection (ATCC), 10801 University Blvd., Manassas, Va. 20110.

"Xylose" refers to xylo-pentose and its derivatives, occurring primarily as D-xylopyranose in xylans and xyloglucans.

"Yeast" refers to a unicellular fungus that has a single nucleus and reproduces either asexually by budding and transverse division or sexually through spore formation.

DETAILED DESCRIPTION

I. Introduction

The present invention relates to yeasts capable of fermenting cellulose and hexoses to ethanol, methods for isolating such yeasts, and methods for employing such yeasts for generating ethanol from cellulose- or hemicellulose-containing materials such as paper sludges. Yeasts capable of fermenting such carbon sources may be isolated from a variety of cellulose-containing waste materials. Once isolated, the yeasts are typically identified by molecular phylogenetic techniques, as well as by their physiological properties. Pure cultures of these yeasts may then be employed to quantitatively convert cellulose or hydrolyzed hemicellulose into ethanol.

General methods for culturing, manipulating, and analyzing yeast may be found in Guthrie and Fink, *Methods in Enzymology* v. 194 (Academic Press, NY, 1991) and similar reference works. Methods for manipulating *Saccharomyces cerevisiae* are generally applicable to the *Kluyveromyces* strains of the present invention.

II. Isolation of Pentose-Hexose- and Cellulose-Metabolizing Yeast Strains from Natural and Industrial Source Materials A. Source Materials for Isolation Naturally occurring yeast strains which metabolize pentoses, hexoses, and cellulose may be isolated from a variety of sources. Typically, the source material is an aqueous medium containing cellulose, hemicellulose, or their breakdown products, in which microorganisms with the ability to metabolize pentoses, hexoses, and cellulose may thrive. Industrial waste materials, in which the bioavailability of the cellulose or hemicellulose has been improved by mechanical or chemical processing (e.g., paper pulping), or where cellulose and hemicellulose have been partially or completely hydrolyzed to yield a mixture of hexoses and pentoses, are particularly suitable sources for isolating the yeasts of the invention. Waste materials typically have been exposed to the natural environment (e.g., in a treatment lagoon) which allows colonization of the waste material by the yeasts of the invention. Examples of such materials include bagasse from sugar cane and other crops, rice fibers, oat hulls, corn stover, wheat straw, as well as spent brewer's grains and liquors. A preferred source for isolation of pentose- and cellulose-metabolizing yeast is sludge generated from paper processing, especially recycled paper sludge. Due to the mechanical and chemical disruption of fibers during the pulping process, waste sludge from paper manufacturing is significantly more accessible to hydrolysis as compared to the mostly crystalline form found in native plant material (see Lark et al., *Biomass Bioenergy* 12:135-43 (1997); Duff et al., *Can J Chem Engin* 72:1013-1020 (1994)). Accordingly, sludge from papermaking operations is hospitable to colonization by the yeasts of the invention, and cellulose-, hexose-, and pentose-metabolizing yeasts may be reproducibly isolated from such waste materials.

B. Enrichment Procedures

Depending on the environment to which the source material has been exposed, the source material may contain, in addition to the yeasts of the invention, bacteria, protozoans, and other fungi which may metabolize pentoses and cellulosic materials. The presence of these other microorganisms does not interfere with isolation of the yeasts of the present invention; samples of waste material can be cultured directly on standard yeast media or on carbon-source selective media, and the pentose- or cellulose-metabolizing yeasts may be isolated and identified by morphological, physiological, or molecular characteristics. However, to simplify the isolation procedure, or to isolate yeasts present at low concentrations in the source material, the source material may be inoculated into an enrichment medium (typically in liquid form) that favors the growth of the desired yeasts. Enrichment media may select for yeast at the expense of other microorganisms, and/or may comprise a particular saccharide as the sole carbon source to select for yeast able to metabolize the desired saccharide. To select for yeasts, particularly thermotolerant yeasts, enrichment media typically contain a high concentration of glucose, are acidic, and are incubated at high temperatures (about 40° C. to 45° C.). Thus, a typical yeast enrichment medium consists of about 50 mM citrate buffer, pH about 4.5, about 20% glucose, about 2% peptone, and about 1% yeast extract, and enrichment takes place by inoculating the enrichment medium with a waste sample and incubating for about 18 hours at about 45° C. Enrichment media may also contain a particular saccharide derivative in place of glucose (e.g., a hexose, a pentose, cellulose derivative, or hemicellulose derivative) to enrich for yeasts that can utilize the saccharide derivative as a carbon source.

C. Isolation of Biologically Pure Cultures and Phenotypic Selection

A biologically pure culture is typically a population of organisms with identical characteristics, or a clonal population derived from a single founder cell. Thus, to generate a biologically pure culture of yeast from a source material or enrichment culture, one typically performs a culture procedure in which a population of cells is derived from a single founder cell physically separated from other cells. Examples of such procedures include streaking or plating for single colonies on solid substrates, or cloning by limiting dilution in liquid media. Phenotypic selection occurs by testing a sample of yeast, derived either directly from source material or from an enrichment culture, for the desired physiological property. Typically, the desired physiological property is metabolism or fermentation of a particular carbon source (e.g., cellulose or a pentose). For example, in one embodiment of the invention, yeasts metabolizing cellulose or pentoses are identified by their ability to grow on agar plates or liquid medium containing only cellulose, or only a pentose, as the carbon source. Alternatively, the ability of the yeast to ferment a cellulose may be determined by culturing the yeast in a medium containing the saccharide of interest and monitoring the production of ethanol.

Isolation may be carried out prior to phenotypic selection, concurrently with phenotypic selection, or after phenotypic selection. For example, isolation may be performed prior to phenotypic selection by plating samples of source material or enrichment culture on YPD plates, as in Example 1. Cultures derived from single colonies are then selected for their saccharide growth or fermentation properties, as described in Examples 2 and 3. In an alternative embodiment, concurrent isolation and phenotypic selection may be performed by inoculating a sample of the source material or enrichment culture directly onto a plate containing a particular carbon source. For example, samples of source material or enrichment culture may be spread on plates containing only cellulose or a pentose as a carbon source, and biologically pure cultures isolated from single colonies arising on the selective plate. Finally, isolation of a pure culture may be performed after phenotypic selection. In this embodiment, samples of source material or enrichment culture are grown in medium containing cellulose or a pentose as a carbon source without any attempt to isolate single colonies. Following growth in the selective media, the yeasts are plated on selective or non-selective plates to isolate biologically pure cultures from single colonies.

III. Characterization of Isolated Yeast Strains

Once the desired yeast strain is isolated, its identifying characteristics may be determined by a number of physiological and molecular means. Molecular characterization of isolated strains is performed by analysis of particular nucleic acids, proteins, or other molecules that differentiate one yeast strain from another. Physiological characterization typically identifies the strain by its ability to grow on, assimilate, or ferment various organic substrates.

A. Molecular Characterization

Figure 1B:
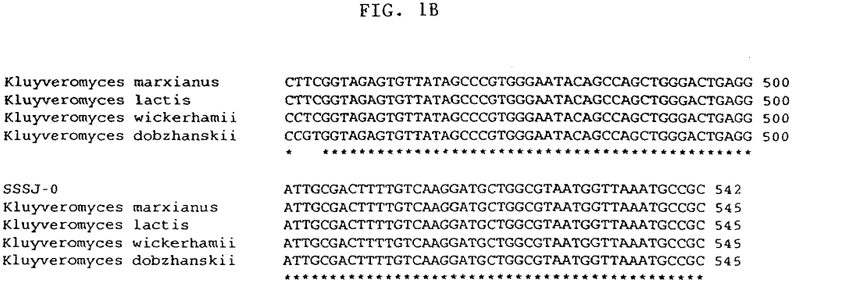
FIG. 1 illustrates an alignment comparing the sequence of the D1/D2 variable region of the 26S ribosomal DNA among isolate SSSJ-0, *Kluyveromyces marxianus*, *K. lactis*, *K. wickerhamii*, and *K. dobzhanskii*.

A preferred method to characterize isolated yeasts is to sequence a portion of the nuclear large subunit (26S) ribosomal DNA. Divergence in the variable D1/D2 domain of the large subunit is generally sufficient to resolve individual species of ascomycetous yeasts (Kurtzman & Robnett, *Antonie van Leeuwenhoek* 73:331-71 (1998)). The D1/D2 sequence may be determined by isolating DNA from a biologically pure yeast sample, amplifying the DNA with primers hybridizing to conserved sequences that flank the D1/D2 region, isolating and sequencing the amplification product, and comparing the sequence of the amplification product to the D1/D2 sequence of known yeasts. Accordingly, in one embodiment, DNA is isolated from an isolated yeast strain and amplified with the primers NL-1 (SEQ ID NO: 2) and NL-4 (SEQ ID NO: 3) of Kurtzman & Robnett. The resulting D1/D2 sequence of isolate SSSJ-0, a cellulose- and pentose-metabolizing strain isolated by the methods disclosed herein and identified as a strain of *Kluyveromyces marxianus* by its D1/D2 sequence, is shown as SEQ ID NO: 1.

Other methodologies for identifying isolated strains do not require direct sequencing of a characteristic nucleic acid. For example, closely related *Kluyveromyces* strains may be distinguished by analyzing restriction fragment length polymorphisms (RFLPs) in the non-transcribed spacer 2 region of the ribosomal DNA (Nguyen et al., *Can J Microbiol* 46:1115-22 (2000)). In addition, randomly amplified polymorphic DNA (RAPD) analysis may be employed to differentiate between many different species of yeast from a variety of genera (Andrighetto et al., *Lett Appl Microbiol* 30:5-9 (2000); Prillinger et al., *Antonie van Leeuwenhoek* 75:267-83 (1999)).

B. Physiological Characterization

Yeasts may also be identified characterized by their morphology or physiological characteristics. Physiological characterization typically includes fermentation of sugars, assimilation of various carbon compounds, assimilation of nitrogen compounds, vitamin requirements, temperature tolerance, sensitivity to protein synthesis inhibitors, and splitting of urea (see van der Walt & Yarrow, in The Yeasts—A Taxonomic Study ed. Kreger-van Rij, N. J. W., pp. 45-104, Amsterdam: Elsevier (1984); Barnett et al., Yeasts: Characteristics and Identification 3rd ed., Cambridge: Cambridge University Press (2000)). Differential sensitivity to the toxins produced by a panel of killer yeasts may also be used to identify isolated yeast cultures (Buzzini & Martini, *Sys Appl Microbiol* 23:450-7 (2000)).

IV. Degradation of Cellulose and Fermentation of Cellulose and Hemicellulose Hydrolysates Bioconversion of cellulosic material to ethanol by the methods of the present invention usually involves pretreatment, saccharification to fermentable sugars, and fermentation of the sugars to ethanol. Not all steps are essential for every embodiment. For example, paper and hydrolysis waste streams may require little pretreatment before saccharification, while treatments aimed solely at decreasing the insoluble content of waste materials may dispense with fermentation.

A. Starting Materials Comprising Plant Saccharides

Sources of cellulose and hemicellulose suitable for fermentation to ethanol by the methods of the invention include such sources as hardwoods, softwoods, pulps and sludges from papermaking and other processes, fibrous raw materials derived from agriculture (bagasse, rice fibers, oat hulls, corn stover, wheat straw, bast fibers, and the like) and spent grains and liquors from brewing and distilling operations. Starting materials obtained as a sludge, liquor, or slurry may vary widely in the amount of saccharide present, depending on the industrial process and treatment steps. Solids in paper sludge typically contain from about 7% to about 23% dry material, of which about 68% is cellulose. Cellulose content of complex biological materials can be determined by a combination of extraction and analytic steps that separate cellulose from associated materials (see Updegraff, *Analytical Biochem* 32:420-4 (1969)). The amount of cellulosic material or other saccharide in the starting material may easily be adjusted by diluting or dehydrating the source material.

B. Pretreatment of Cellulose- and Hemicellulose-Containing Materials

Industrial wastes such as pulps and sludges are advantageous in that they often have been subjected to mechanical or chemical processes which increase the bioavailability of cellulose and hemicellulose. For other materials, pretreatment is desirable to increase the accessibility of the polymers to hydrolytic enzymes and to dissociate cellulose, hemicellulose, and lignin components from each other. Pretreatments include mechanical size reduction, heat, steam, steam explosion, chemical pulping, solvent extraction, and various combinations of these separate processes. Sulfur dioxide is often used in combination with autohydrolysis because it gives better sugar yields and helps to modify lignin for subsequent extraction or recovery. Sulfur dioxide combined with steam is particularly effective as a pretreatment for enzymatic cellulose saccharification. In general, the purpose of pretreatment is to maximize subsequent bioconversion yields and minimize the formation of inhibitory compounds; see Cowling & Kirk, *Biotech Bioeng Symp* 6:95-123 (1975); Wood & Saddler, in Wood & Kellog eds., *Methods in Enzymology* v. 160, pp. 3-11 (Academic Press, San Diego, 1988).

C. Saccharification

Saccharification is the process of hydrolyzing polymers of the source material, such as cellulose and hemicellulose, or starch, into fermentable mono- and di-saccharides such as cellobiose, glucose, xylose, arabinose, mannose, and galactose. For cellulosics, methods for saccharification include autohydrolysis, acid hydrolysis, and enzymatic hydrolysis.

1. Acid Hydrolysis

Autohydrolysis is the process of converting cellulosic materials into fermentable sugars by exposure to high temperature steam. Many lignocellulosic materials contain significant quantities of acetylated hemicellulose. Steam releases these in the form of acetic acid which subsequently carries out a partial hydrolysis of the hemicellulosic and cellulosic sugars. Sugar yields are generally lower than treatments involving addition of exogenous acids.

Acid hydrolysis is often used as a pretreatment because it can be adapted to a wide variety of feedstocks. Except in the case of strong hydrochloric acid hydrolysis, it is generally carried out at elevated temperature (100 to 240° C.) for various lengths of time. At higher acid concentrations, it can be carried out at temperatures as low as 30° C. Sulfuric acid can be used in concentrated form, but it is far more commonly used in a dilute solution of 0.5 to 5% sulfuric acid (on a w/w basis with dry solids). The concentrated form usually employs a method of separating and recycling the acid catalyst limiting the total acid losses to approximately 3%, or the same as the dilute process. Use of the concentrated acid however, allows lower temperature and pressure hydrolysis with fewer byproducts produced. Concentrated hydrochloric acid (47%) is sometimes used for strong acid hydrolysis because it is relatively easy to recover. Hydrolysis with concentrated hydrochloric acid gives one of the highest sugar yields of any acid hydrolysis process. It is carried out at room temperature. The chief drawback is the difficulty in handling and recovering the hydrochloric acid.

Dilute acid hydrolysis with 1 to 5% sulfuric acid is generally considered the most cost-effective means of hydrolyzing wood and agricultural residues. Yields of hemicellulosic sugars can be 80 to 95% of theoretical. Yields of glucose from cellulose are generally less than 50% but can approach 55% at elevated temperatures. Percolating and two-step dilute acid processes are suitable for yielding fermentable sugars from most materials (see Durbak et al., "Wood", in *Kirk-Othmer Encyclopedia of Chemical Technology* 4th ed., John Wiley & Sons, New York, 1998).

2. Enzymatic Hydrolysis

Fermentable sugars may also be released from cellulosic materials by enzymatic hydrolysis. In such embodiments, cellulose or hemicellulose is treated with hydrolytic enzymes that release mono- or disaccharides from cellulose or hemicellulose. Typically originating in wood-rotting fungi or bacteria, enzymes may be added as purified polypeptides which possess a single cellulolytic activity, or as complexes or mixtures typically isolated from a wood-degrading organism and comprising several cellulolytic activities residing on different polypeptides. For cellulose, complete cellulase activity usually requires the activity of endo-1,4-β-glucanases, which hydrolyze cellulose chains at random, cellobiohydrolases or exo-1,4-β-glucanases, which remove glucose or cellobiose from the non-reducing end of the chain, and β-glucosidases, which hydrolyze to glucose the short-chain cell oligosaccharides and cellobiose which are released by other enzymes. *K. marxianus* strains are capable of fermenting cellobiose directly, so addition of β-glucosidases is not strictly necessary for saccharification. Enzymes liberating fermentable sugars from hemicellulose include xylanases, β-mannases, β-glucosidases, and arabinofuranosidases and arabinogalactases. Where the source material contains starch, amylases are employed to hydrolyze the starch.

Enzymatic saccharification may be performed prior to fermentation, in which case saccharification may proceed at the optimal temperature for the hydrolytic enzymes (e.g., 50° C.). However, simultaneous saccharification and fermentation by yeast is desirable to simplify the procedure. For organisms such as *Saccharomyces cerevisiae*, saccharification must take place well below optimal temperatures due to the relatively low thermotolerance of the yeast (see Duff et al., *Can J Chem Engin* 72:1013-1020); for more heat-resistant organisms such as *K. marxianus*, simultaneous saccharification and fermentation may be carried out closer to the optimum saccharification temperature (e.g., 43-45° C.).

An alternative strategy for enzymatic saccharification is to culture the treated source material with a living organism able to degrade the cellulosic materials to fermentable sugars. Such organisms typically produce hydrolytic enzymes capable of partially or complete breaking down the polymers to fermentable sugars. Co-culture or pretreatment with a cellulolytic organism may be employed to saccharify source materials. In one embodiment of the invention, however, the same organism is employed to hydrolyze the cellulosic material and to ferment the resulting sugars. For example, *K. marxianus* strain SSSJ-0 is capable of both breaking down cellulose and fermenting the breakdown products. Thus, strains such as SSSJ-0 may employed in single-step saccharification and fermentation procedures without the addition of cellulolytic enzymes, although exogenous enzymes may be added to speed saccharification or to saccharify polymers that the yeast cannot hydrolyze. Such procedures may be carried out under a single set of reaction conditions. Alternatively, the optimal culture conditions (e.g., temperature, pH, osmotic pressure, oxygen concentration, etc.) for saccharification and fermentation may be determined empirically, and each step carried out with maximum efficiency by appropriate adjustment of the medium or culture conditions between the steps.

D. Hydrolysate Fermentation

Once a hydrolysate has been generated, the sugars in the hydrolysate are cultured with a yeast of the invention to yield ethanol. The composition of the hydrolysate will depend on the source material and the completeness with which the cellulosic materials have been hydrolyzed. Hydrolysis of cellulose yields primarily glucose and cellobiose. Hydrolysis of the hemicelluloses will yield various sugars, the predominant forms depending on the ratios of xylan (yielding primarily xylose, arabinose, and small amounts of glucose, galactose, and mannose), glucomannans (yielding primarily glucose, galactose, and mannose) and xyloglucans (yielding primarily glucose, xylose, galactose, and arabinose). Thus, while varying amounts of other components may be present, hydrolysis of lignocellulosic materials will usually yield a mixture of saccharides, comprising the hexoses glucose, galactose, mannose and the disaccharide cellobiose, as well as the pentoses xylose and arabinose. Accordingly, fermentation usually begins with a mixture of hexoses and pentoses in an aqueous medium either present in the starting material (e.g., sludge) or added to dry source materials during pretreatment or saccharification.

Optimal culture conditions may vary depending on the type and concentration of source material and the pretreatment procedure (see Banat et al., *World J Microbiol & Biotechnol* 14:809-21 (1998) and Singh et al., *World J Microbiol & Biotechnol* 14:823-34 (1998) for review). Optimal conditions may be determined empirically simply by varying a particular parameter (e.g., carbon source concentration) over a range of values and determining the optimal yield of ethanol for each condition.

Typical conditions for fermentation of hexoses by *K. marxianus* strain SSSJ-0 are culture at about 43-45° C. in a medium comprising less than about 20% solid material, and supplemented with about 50 mM citrate buffer, pH about 4.5, about 0.25 mM magnesium sulfate, and about 6.7 g/L yeast nitrogen base. Minerals, vitamins and other small organic molecules, and supplemental carbon sources may be added to the culture medium to promote growth, fermentation, or ethanol tolerance. Other convenient sources of nitrogen compounds known in the art to support yeast growth and fermentation may be employed, e.g., corn steep liquor or diaminophosphate.

To provide an inoculum for the fermentation vessel, seed cultures of yeast are typically generated by overnight growth and added in mid-log phase at a dilution of 1:50, although other culture dilutions may be suitable depending on fermentation conditions and reactor design. The seed culture may be grown in a medium comprising a particular carbon source (e.g., xylose or carboxymethylcellulose) in order to induce hydrolytic or fermentative enzymes prior to inoculation in the fermentation vessel (see, e.g., Jeffries et al, *Biotechnol Bioengin* 31:502-506 (1988)).

Standard fermentation vessels and systems for yeast culture are suitable for fermentation of plant saccharides. As carbon dioxide production will affect the pH of the culture medium, pH of the culture may be maintained at about 4.5 by typical fermentation methods, e.g., automatic addition of acid or base triggered by a pH sensor. Fermentation may take place aerobically or anaerobically. Anaerobic fermentations may ultimately yield less ethanol, but in applications where the heat generated by fermentation is problematic, anaerobic fermentation is preferred. A period of aerobic growth may be desirable to rapidly increase cell mass before anaerobic fermentation begins. Anaerobic conditions may be obtained by removing oxygen from the medium prior to culture, or simply by sealing the culture vessel and allowing the yeasts to naturally exhaust the oxygen supply. In either circumstances, culture vessels are typically vented to relieve pressure generated from carbon dioxide buildup during fermentation.

In some embodiments, the hydrolysate is fermented in a closed system without removal of biomass or fermented medium, e.g., batch or batch-fed culture systems. Under these circumstances, fermentation typically proceeds until the sugar supply is exhausted or until the buildup of ethanol terminates fermentation. In batch-fed systems, new medium and, optionally, yeast, may be added to continue fermentation. Ethanol tolerance depends on strain background, medium composition, and temperature, but is typically about 8% for *K. marxianus* before the ethanol production rate begins to decline (see Banat et al., *World J Microbiol & Biotechnol* 14:809-21 (1998)).

Hydrolysate fermentation may also take place in a variety of bioreactor systems. In one embodiment, fermentation takes place under steady-state culture conditions, in which carbon sources are added and ethanol and cells removed from the culture vessel at constant rates such that the composition of the culture medium remains unchanged. The advantage of such systems is that inhibitory effects of high sugar and ethanol concentrations may be avoided. However, where the cells divide slowly under fermentative conditions, maintenance of the culture biomass may be difficult. Accordingly, a variety of immobilized cell bioreactors may be employed. In such bioreactors, the biomass of cells remains in the reactor, but a constant influx of hydrolysate and removal of ethanol by medium circulation keeps culture conditions constant. For *K. marxianus*, flocculent strains may be readily isolated, and simple bioreactors which recycle cells by natural sedimentation of flocculating yeast may be employed (see Teixeira et al., *Bioprocess Engin* 5:123-7 (1990)). Alternatively, yeasts may be immobilized in or on solid supports such as calcium alginate beads, kissiris, polyvinyl alcohol cryogels, or porous ceramics, and incorporated into continuous or fed batch bioreactor designs (see Banat et al., *World J Microbiol & Biotechnol* 14:809-21 (1998); Singh et al., *World J Microbiol & Biotechnol* 14:823-34 (1998)). Finally, yeast may be immobilized on a variety of reactor surfaces by formation of biofilms, thereby maximizing the surface area available for interaction of the biomass and culture medium.

The progress of fermentation or hydrolysis may be monitored by measuring the total or reducing sugar content of the hydrolysate, measuring the carbon dioxide evolved by the culture, or by measuring the amount of ethanol in the medium. Ethanol present in the fermentation medium may be measured by physical (e.g., by HPLC or gas chromatography) or enzymatic techniques (e.g., alcohol dehydrogenase and NAD; see Bernt & Gutmmann, in Bergmeyer, ed., *Methods of Enzymatic Analysis* 2d ed., pp. 1499-1502. Academic Press, NY (1974)). Fermentation may be quantified by determining the ethanol concentration at a fixed time point or when fermentation ceases, or by measuring the initial or steady-state rate of ethanol production. Once the desired quantity of ethanol has been generated, it may be recovered or extracted from the medium by ordinary means (e.g., distillation, extraction, membrane separation, or water adsorption).

EXAMPLES

The following examples are offered to illustrate, but not to limit the claimed invention.

Example 1

Isolation of Strain SSSJ-0 by Enrichment Culture from Recycled Paper Sludge Recycled paper sludge was obtained from the Smurfit-Stone Container Corporation, Santa Clara, Calif. A sample of the sludge (0.4 g) was inoculated into an enrichment culture medium composed of 50 mM citrate buffer, pH 4.5, 20 percent glucose, 2 percent peptone, and 1 percent yeast extract. The culture was maintained at 45° C. in a shaking water bath (100 rpm) for 18 hours. An aliquot of the enrichment culture was then spread onto plates of YPD, a medium composed of 1 percent yeast extract, 2 percent peptone, 2 percent glucose, and 2 percent agar. The plates were cultured at 43° C. for 18 hours, by which time single colonies of yeast appeared. A single yeast colony was picked and propagated on YPD plates as strain SSSJ-0.

Example 2

Identification of Strain SSSJ-0 as a Variant of Kluyveromyces marxianus

The yeast strain recovered by the enrichment method was identified by sequencing the D1/D2 region of the 18S ribosomal DNA (Kurtzman & Robnett, *Antonie van Leeuwenhoek* 73:331-371 (1998)). Genomic DNA was extracted from a ~1 mm² colony of the sample using a chelex resin (Walsh et al., *Biotechniques* 10:506-513 (1991)). The D1/D2 region of the 18S ribosomal DNA was amplified by the polymerase chain reaction (PCR) using the primers NL-1 (5'-GCATAT-CAATAAGCGGAGGAAAAG) and NL-4 (5'-GGTCCGT-GTTTCAAGACGG). The PCR was performed with Taq DNA polymerase (Promega), using the conditions recommended by the manufacturer, in a PTC-200 thermal cycler (MJ Research). PCR products were visualized on a 1% agarose (SeaKem) gel and cleaned using a PCR purification kit from Qiagen. Cleaned PCR products were sent for automated DNA sequencing at Davis Sequencing LLC. The amplification products had the sequence shown in SEQ ID NO: 1. Based on this sequence, the strain of yeast was identified as *K. marxianus* using CLUSTALW alignment with yeast DNA sequences obtained from Genbank (http://www.ncbi.nlm.nih.gov/).

Example 3

Growth of Strain SSSJ-0 on Plant Saccharides

Seed cultures of SSSJ-0 were grown at 43° C. in a liquid medium composed of 20 g/L glucose, 0.67 g/L yeast nitrogen base, and 0.25 mM magnesium sulfate in a 50 mM citrate buffer, pH 4.5. Mid-log aliquots of the seed culture were inoculated (1:50) into test media of identical composition but containing 20 g/L of the carbon source instead of glucose. The amount of carbon source in the recycled paper sludge was estimated by determining the cellulose content of a dried sample. The cultures were maintained at 43° C. in shaking water baths (100 rpm). The increase in cell number was determined by measuring the OD600 of the cultures, or, in the case of the insoluble cellulosics, by plating aliquots of the culture on YPD plates and scoring the number of colonies developed. The doubling time of SSSJ-0 was determined by plotting the number of cells as a function of time in culture.

| Carbon Source | Doubling Time (hours) |
| --- | --- |
| Glucose | 4.0 |
| Arabinose | 4.5 |
| Xylose | 7.5 |
| Galactose | 4.0-4.5 |
| Mannose | 4.0-4.5 |
| Cellobiose | 3.5 |
| Carboxymethylcellulose | 4.0 |
| AVICEL ® | 10.0 |
| SIGMACELL ® | 10.0 |
| Recycled paper sludge | 6.0 |

Example 4

Growth of Strain SSSJ-0 on Various Carbon Sources

Figure 2:
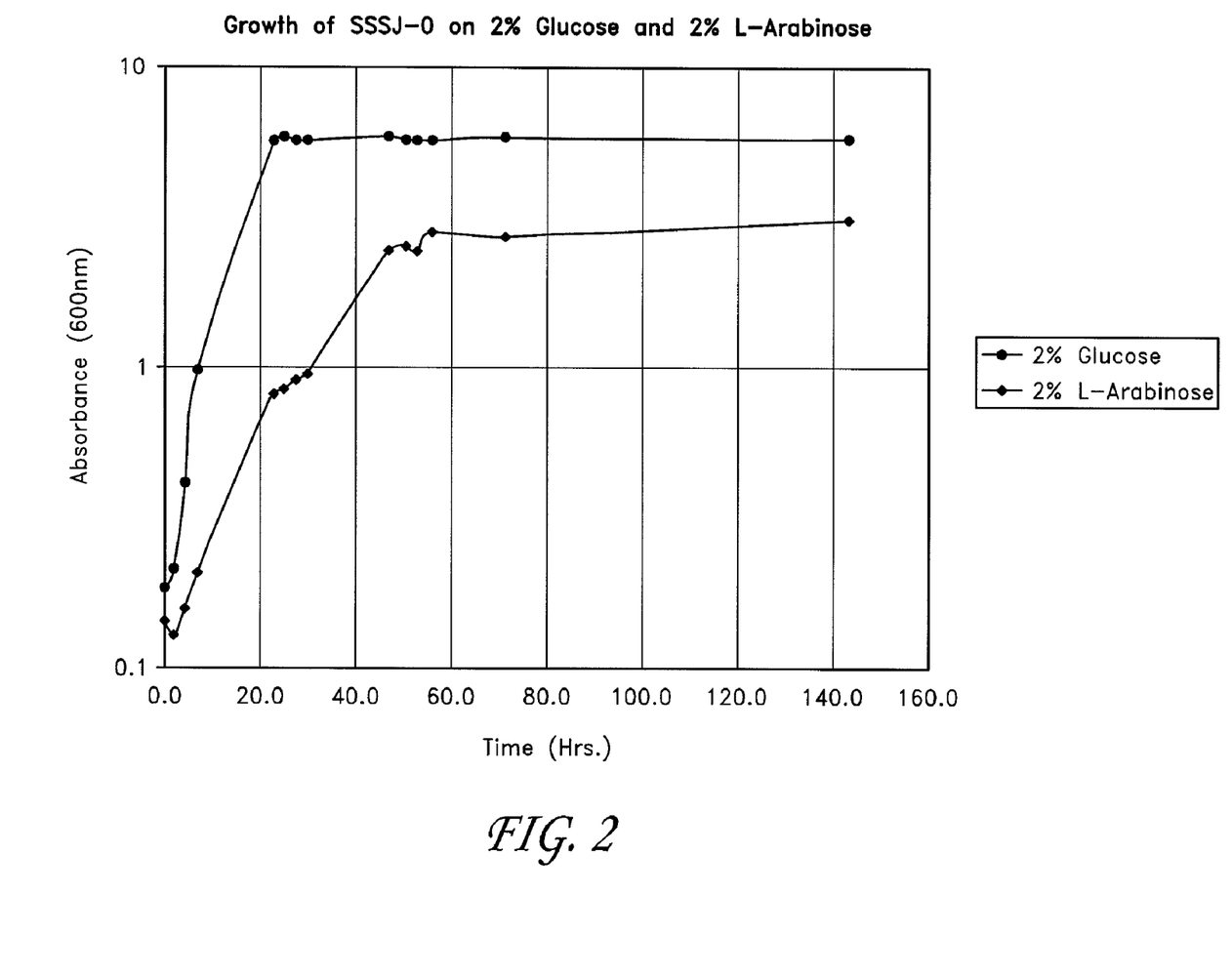
FIG. 2 illustrates growth (i.e., proliferation) of SSSJ-0 on 2% glucose and 2% L-arabinose.
Figure 3:
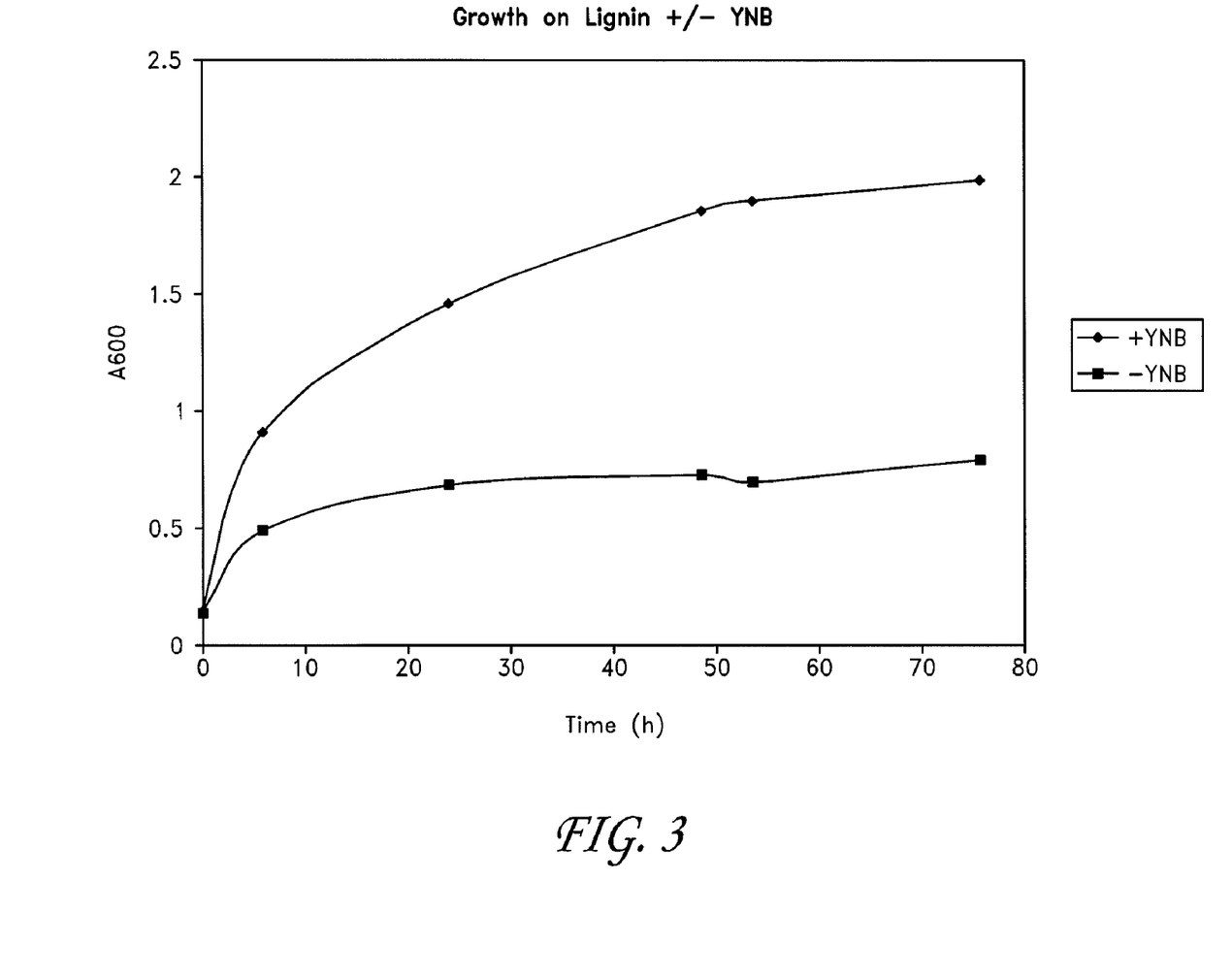
FIG. 3 illustrates growth (i.e., proliferation) of SSSJ-0 on 2% lignin in the presence and absence of yeast nitrogen base (0.67 g/L).
Figure 4:
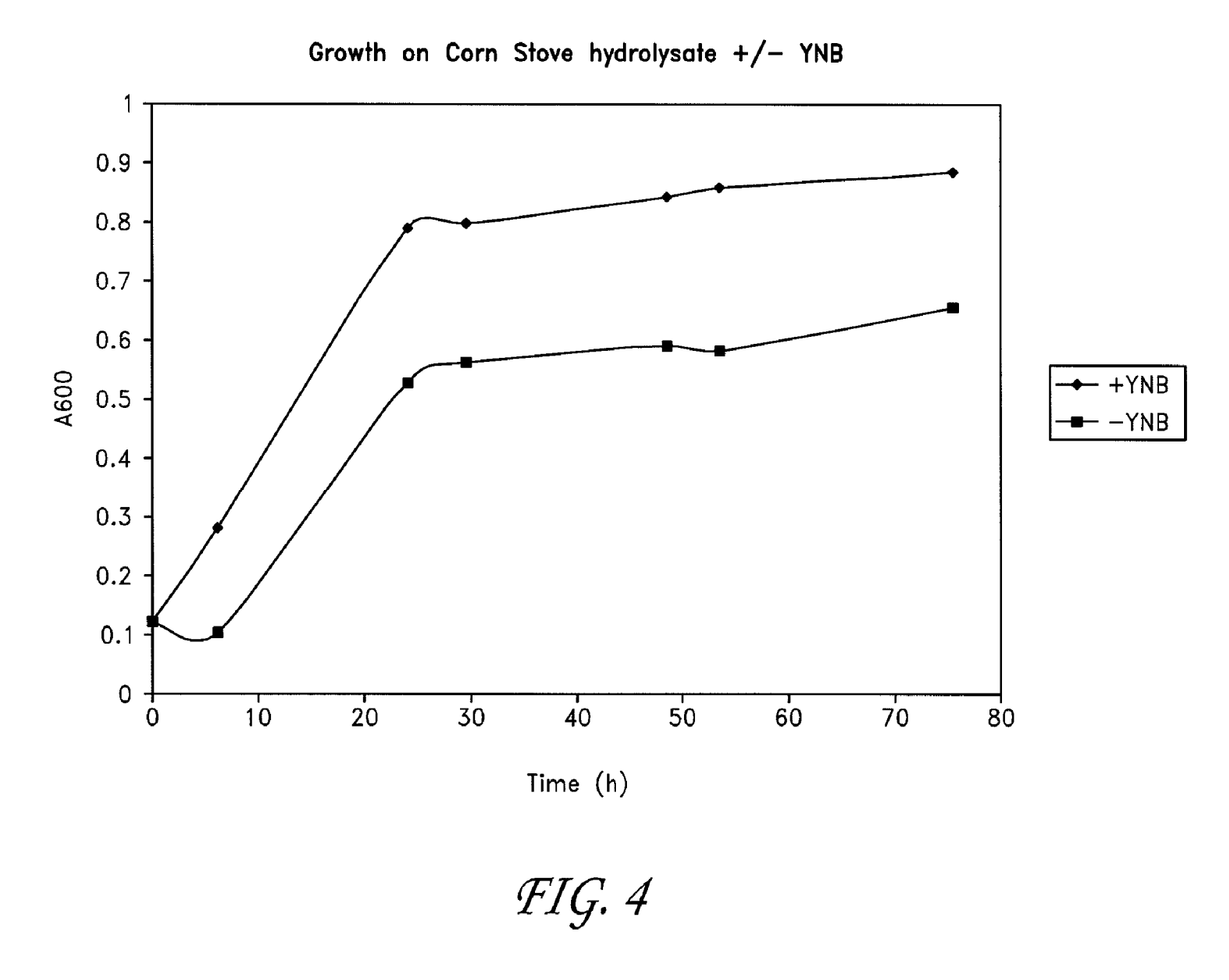
FIG. 4 illustrates growth (i.e., proliferation) of SSSJ-0 on 2% corn stover hydrolysate in the presence and absence of yeast nitrogen base (0.67 g/L).
Figure 5:
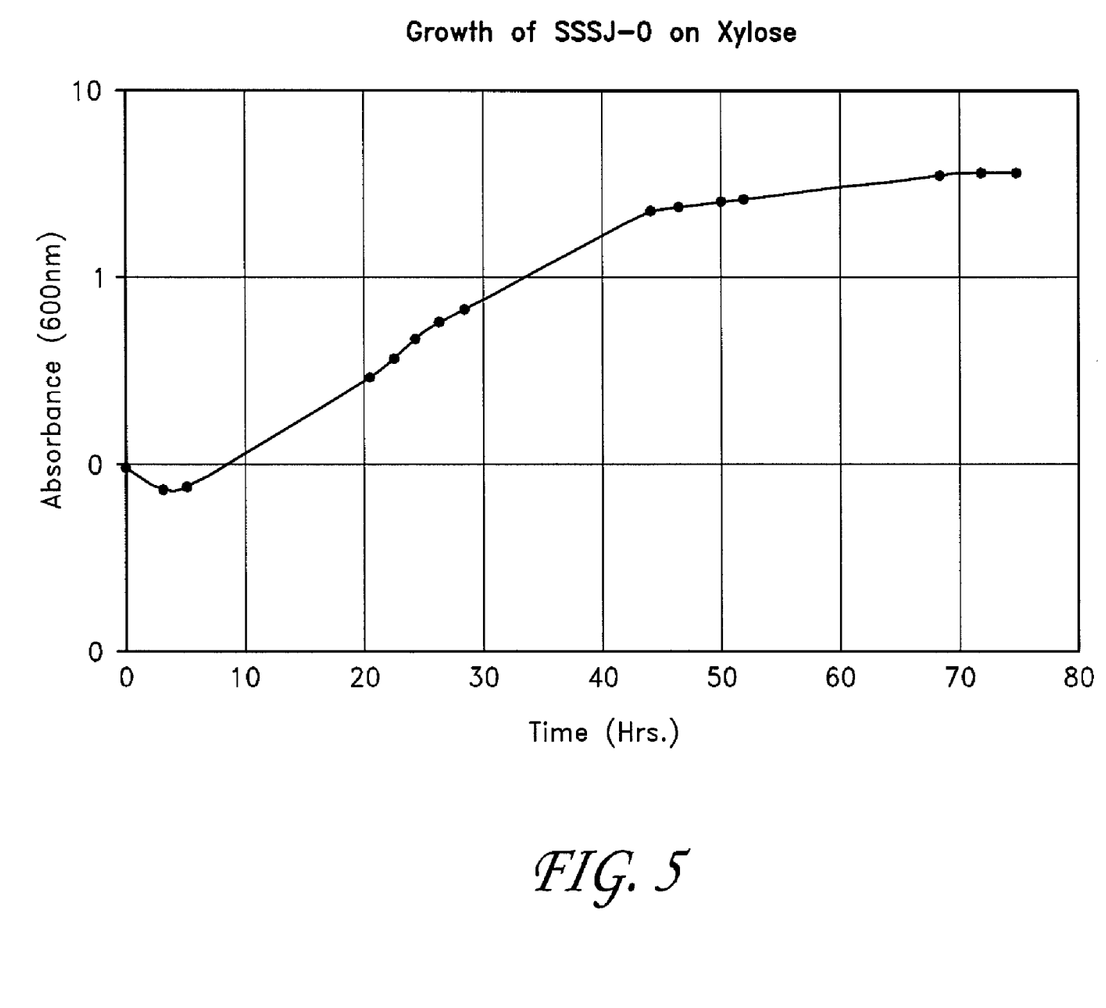
FIG. 5 illustrates growth (i.e., proliferation) of 2% xylose.
Figure 6:
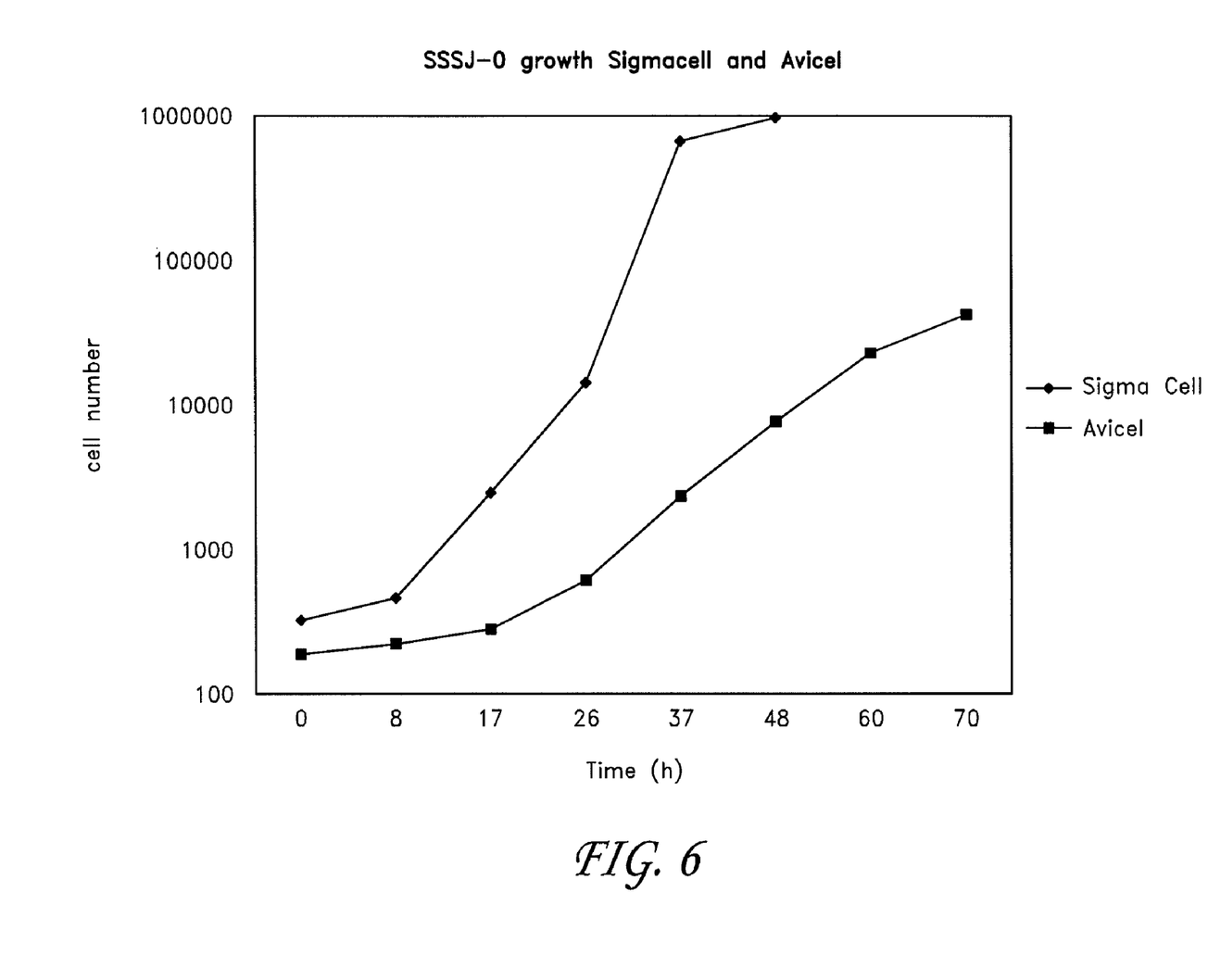
FIG. 6 illustrates growth (i.e., proliferation) of SSSJ-0 on 2% SIGMACELL® and 2% AVICEL®.

Seed cultures of SSSJ-0 were grown and inoculated into media containing (1) 2% glucose and 2% L-arabinose; (2) 2% lignin+/−0.67 g/L yeast nitrogen base (Fisher); (3) 2% corn stover hydrolysate+/−0.67 g/L yeast nitrogen base; (4) 2% xylose; and (5) 2% SIGMACELL® or 2% AVICEL®, according to the method of Example 3. The increase in cell number was determined by measuring the OD600 of the cultures, or, in the case of the SIGMACELL® (Sigma) and AVICEL® (Fluka), by plating aliquots of the culture on YPD plates and scoring the number of colonies developed. Results of SSSJ-0 growth on 2% glucose and 2% L-arabinose are shown in FIG. 2. Results of SSSJ-0 growth on lignin+/−yeast nitrogen base are shown in FIG. 3. Results of SSSJ-0 growth on corn stover hydrolysate+/−yeast nitrogen base are shown in FIG. 4. Results of SSSJ-0 growth on xylose are shown in FIG. 5. Results of SSSJ-0 growth on SIGMACELL® or AVICEL® are shown in FIG. 6.

Example 5

Production of Ethanol by Fermentation of Plant Saccharides

Seed cultures of SSSJ-0 were grown and inoculated into media containing plant saccharides according to the method of Example 3, except that the test cultures were grown in air-tight serum bottles to promote anaerobic fermentation. After 48 hours, an aliquot of the medium was withdrawn and enzymatically assayed for ethanol content by incubation with alcohol dehydrogenase and NAD.

| Carbon Source | Ethanol (mg/L) |
| --- | --- |
| Glucose | 67.0 |
| Arabinose | 4.6 |
| Xylose | 6.4 |
| Galactose | 21.2 |
| Mannose | 18.9 |
| Cellobiose | 3.9 |
| Carboxymethylcellulose | 4.6 |
| AVICEL ® | 2.0 |

-continued

| Carbon Source | Ethanol (mg/L) |
|---|---|
| SIGMACELL® | 6.1 |
| Brewers spent grain (wet) | 5.0 |
| Recycled paper sludge | 6.1 |

Example 6

Production of Ethanol from Paper Sludge by Enzyme-Free Simultaneous Saccharification and Fermentation Paper sludge was obtained from a plant in Ohio. Seed cultures of SSSJ-0 were grown overnight in citrate buffer, pH 4.5 with yeast nitrogen base, magnesium sulfate, and 2% carboxymethylcellulose. The seed culture was inoculated at a dilution of 1:500 into 20 ml of a culture medium composed of citrate buffer with yeast nitrogen base, magnesium sulfate, and sludge containing about 350 mg of cellulose. The culture was grown in an air-tight serum bottle at 43° C. in a shaking water bath. After 48 hours, an aliquot of the medium was removed and assayed for ethanol content with alcohol hydrogenase and NAD. The aliquot contained 125 mg/L of ethanol.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing ethanol from an aqueous medium comprising a saccharide selected from the group consisting of cellobiose, glucose, mannose, galactose, and combinations thereof, the method comprising the steps of
   (a) contacting an aqueous medium comprising a saccharide selected from the group consisting of cellobiose, glucose, mannose, galactose, and combinations thereof, with *Kluyveromyces marxianus* strain SSSJ-0 having ATCC Accession No. PTA-3567 deposited on Jul. 26, 2001; and
   (b) incubating the aqueous medium under conditions wherein the saccharide is fermented to ethanol.

2. The method of claim 1, further comprising the step of recovering the ethanol.

3. The method of claim 1, wherein the aqueous medium is incubated at a temperature between about 43° C. and about 45° C.

4. A method of producing ethanol from an aqueous medium containing cellulose, the method comprising the steps of
   (a) contacting an aqueous medium containing cellulose with *Kluyveromyces marxianus* strain SSSJ-0 having ATCC Accession No. PTA-3567 deposited on Jul. 26, 2001; and
   (b) incubating the aqueous medium under conditions wherein the cellulose is fermented to ethanol.

5. The method of claim 4, further comprising the step of recovering the ethanol.

6. The method of claim 4, wherein the aqueous medium is incubated at a temperature between about 43° C. and about 45° C.

7. The method of claim 1, wherein the saccharide is produced by hydrolyzing polymers of a saccharide source material prior to step (a).

8. The method of claim 7, wherein the saccharide source material comprises cellulose, hemicellulose, or both.

9. The method of claim 8, wherein the saccharide source material comprises one or more of hardwoods, softwoods, pulps from papermaking processes, sludges from papermaking processes, fibrous raw materials, and spent grains and liquors from brewing or distilling operations.

10. The method of claim 7, wherein the hydrolyzing comprises acid hydrolysis.

11. The method of claim 7, wherein the hydrolyzing comprises enzymatic hydrolysis.

12. The method of claim 1, wherein the saccharide is fermented in a batch or batch-fed culture system.

13. The method of claim 4 wherein the cellulose source material comprises one or more of hardwoods, softwoods, pulps from papermaking processes, sludges from papermaking processes, fibrous raw materials, and spent grains and liquors from brewing or distilling operations.

14. The method of claim 4, wherein the cellulose is fermented in a batch or batch-fed culture system.

\* \* \* \* \*

SEQUENCE LISTING

```
<160> NUMBER OF SEQ ID NOS: 7

<210> SEQ ID NO 1
<211> LENGTH: 542
<212> TYPE: DNA
<213> ORGANISM: Kluyveromyces marxianus strain SSSJ-0
<220> FEATURE:
<221> NAME/KEY: misc_feature
<222> LOCATION: 12, 18
<223> OTHER INFORMATION: n = A,T,C or G

<400> SEQUENCE: 1
ccaaccggga tngccttngt aacggcgagt gaagcggcaa aagctcaaat ttgaaatctg      60
gcgtcttcga cgtccgagtt gtaatttgaa gaaggcgact ttgtagctgg tccttgtcta     120
tgttccttgg aacaggacgt catagagggt gagaatcccg tgtggcgagg atcccagtta     180
tttgtaaagt gcttctcgacg agtcgagttg tttgggaatg cagctctaag tgggtggtaa     240
attccatcta aagctaaata ttggcgagag accgatagcg aacaagtaca gtgatggaaa     300
gatgaaaaga actttgaaaa gagagtgaaa aagtacgtga aattgttgaa agggaagggc      360
atttgatcag acatggcgtt tgcttcggct ttcgctgggc cagcatcagt tttagcggtt      420
ggataaatcc tcgggaatgt ggctctgctt cggtagagtg ttatagcccg tgggaataca     480
gccagctggg actgaggatt gcgacttttg tcaaggatgc tggcgtaatg gttaaatgcc      540
gc                                                                    542

<210> SEQ ID NO 2
<211> LENGTH: 24
<212> TYPE: DNA
<213> ORGANISM: Artificial Sequence
<220> FEATURE:
<223> OTHER INFORMATION: Chemically synthesized D1/D2 primer NL-1

<400> SEQUENCE: 2
gcatatcaat aagcggagga aaag                                             24

<210> SEQ ID NO 3
<211> LENGTH: 19
<212> TYPE: DNA
<213> ORGANISM: Artificial Sequence
<220> FEATURE:
<223> OTHER INFORMATION: Chemically synthesized D1/D2 primer NL-4
```

```
<400> SEQUENCE: 3
ggtccgtgtt tcaagacgg                                                  19

<210> SEQ ID NO 4
<211> LENGTH: 545
<212> TYPE: DNA
<213> ORGANISM: Kluyveromyces marxianus

<400> SEQUENCE: 4
aaaccaaccg ggattgcctt agtaacggcg agtgaagcgg caaaagctca aatttgaaat     60
ctggcgtctt cgacgtccga gttgtaattt gaagaaggcg actttgtagc tggtccttgt    120
ctatgttcct tggaacagga cgtcatagag ggtgagaatc ccgtgtggcg aggatcccag    180
ttatttgtaa agtgctttcg acgagtcgag ttgtttggga atgcagctct aagtgggtgg    240
taaattccat ctaaagctaa atattggcga gagaccgata gcgaacaagt acagtgatgg    300
aaagatgaaa agaactttga aaagagagtg aaaaagtacg tgaaattgtt gaagggaag    360 ggcatttgat cagacatggc gtttgcttcg gctttcgctg gccagcatc agttttagcg    420 gttggataaa tcctcgggaa tgtggctctg cttcggtaga gtgttatagc ccgtgggaat    480
acagccagct gggactgagg attgcgactt ttgtcaagga tgctggcgta atggttaaat    540
gccgc                                                                545

<210> SEQ ID NO 5
<211> LENGTH: 545
<212> TYPE: DNA
<213> ORGANISM: Kluyveromyces lactis

<400> SEQUENCE: 5
aaaccaaccg ggattgcctt agtaacggcg agtgaagcgg caaaagctca aatttgaaat     60
ctggcgtctt cgacgtccga gttgtaattt gaagaaggca actttgtagc tggtccttgt    120
ctatgttcct tggaacagga cgtcatagag ggtgagaatc ccgtgtggcg aggatcccag    180
ttatttgtaa agtgctttcg acgagtcgag ttgtttggga atgcagctct aagtgggtgg    240
taaattccat ctaaagctaa atattggcga gagaccgata gcgaacaagt acagtgatgg    300
aaagatgaaa agaactttga aaagagagtg aaaaagtacg tgaaattgtt gaagggaag    360 ggcatttgat cagacatggc gtttgcttcg gctttcgctg gccagcatc agttttagcg    420 gttggataaa tcctcgggaa tgtggctctg cttcggtaga gtgttatagc ccgtgggaat    480
acagccagct gggactgagg attgcgactt ttgtcaagga tgctggcgta atggttaaat    540
gccgc                                                                545

<210> SEQ ID NO 6
<211> LENGTH: 545
<212> TYPE: DNA
<213> ORGANISM: Kluyveromyces wickerhamii

<400> SEQUENCE: 6
aaaccaaccg ggattgcctt agtaacggcg agtgaagcgg caaaagctca aatttgaaat     60
ctggcgtctt cgacgtccga gttgtaattt gaagaaggta actttgtagc tggtccttgt    120
ctatgttcct tggaacagga cgtcatagag ggtgagaatc ccgtgtggcg aggatcccag    180
ttatatgtaa agtgctttcg acgagtcgag ttgtttggga atgcagctct aagtgggtgg    240
taaattccat ctaaagctaa atattggcga gagaccgata gcgaacaagt acagtgatgg    300
aaagatgaaa agaactttga aaagagagtg aaaaagtacg tgaaattgtt gaagggaag    360
```

-continued

```
ggcatttgat cagacatggc gtttgcttcg gcgttcgctg ggccagcatc agttttagcg    420
gttggataaa tcctcgggaa tgtagctcta cctcggtaga gtgttatagc ccgtgggaat    480
acagccagct gggactgagg attgcgactt ttgtcaagga tgctggcgta atggttaaat    540
gccgc                                                                545

<210> SEQ ID NO 7
<211> LENGTH: 545
<212> TYPE: DNA
<213> ORGANISM: Kluyveromyces dobzhanskii

<400> SEQUENCE: 7
aaaccaaccg ggattgcctt agtaacggcg agtgaagcgg caaaagctca aatttgaaat     60
ctggcgtctt cgacgtccga gttgtaattt gaagaaggtt actttgtagc tggtccttgt    120
ttatgttcct tggaacagga cgtcatagag ggtgagaatc ccgtgtggcg aggataccag    180
ttatatgtaa agtactttcg acgagtcgag ttgtttggga atgcagctct aagtgggtgg    240
taaattccat ctaaagctaa atattggcga gagaccgata gcgaacaagt acagtgatgg    300
aaagatgaaa agaactttga aaagagagtg aaaaagtacg tgaaattgtt gaaagggaag    360
ggcatttgat cagacatggc gtttgcttcg gctttcgctg ggccagcatc agttttggcg    420
gctggataaa tcctcgggaa tgtggctcta ccgtggtaga gtgttatagc ccgtgggaat    480
acagccagct gggactgagg attgcgactt ttgtcaagga tgctggcgta atggttaaat    540
gccgc                                                                545
```